United States Patent
Ramana et al.

(10) Patent No.: US 9,802,909 B2
(45) Date of Patent: Oct. 31, 2017

(54) ENANTIOSELECTIVE PROCESS FOR SYNTHESIS OF (+)- PETROMYROXOL AND ITS DIASTEREOMERS

(71) Applicant: COUNCIL OF SCIENTIFIC & INDUSTRIAL RESEARCH, New Delhi (IN)

(72) Inventors: Chepuri Venkata Ramana, Pune (IN); Venkannababu Mullapudi, Pune (IN)

(73) Assignee: Council of Scientific & Industrial Research, New Dehli (IN)

( * ) Notice: Subject to any disclaimer, the term of this patent is extended or adjusted under 35 U.S.C. 154(b) by 0 days.

(21) Appl. No.: 15/072,949

(22) Filed: Mar. 17, 2016

(65) Prior Publication Data

US 2017/0210720 A1   Jul. 27, 2017

(51) Int. Cl.
*C07D 307/20* (2006.01)

(52) U.S. Cl.
CPC ................................. *C07D 307/20* (2013.01)

(58) Field of Classification Search
CPC .................................................. C07D 307/20
See application file for complete search history.

(56) References Cited

PUBLICATIONS

Boyer, A., "Enantioselective Synthesis of (+)-Petromyroxol, Enabled by Rhodium-Catalyzed Denitrogenation and Rearrangement of a 1-Sulfonyl-1, 2, 3-Triazole." The Journal of organic chemistry 80.9 (2015): 4771-4775.*

Gahalawat, S., "Total Synthesis of (+)-Petromyroxol, a Marine Natural Product." Asian Journal of Organic Chemistry 4.10 (2015): 1025-1029.*

Nookaraju, U., "Total synthesis of (+)-petromyroxol via tandem α-aminoxylation—allylation and asymmetric dihydroxylation—SN 2 cyclization approach." RSC Advances 5.78 (2015): 63311-63317.*

* cited by examiner

*Primary Examiner* — Matt Mauro
(74) *Attorney, Agent, or Firm* — Haug Partners LLP; William S. Frommer

(57) ABSTRACT

An enantioselective process for the synthesis of (+)-petromyroxol and its Diastereomers from (3aR,5R,6aR)-2,2-dimethyl-5-((R)-oxiran-2-yl)tetrahydrofuro[2,3-d][1,3]dioxole.

10 Claims, No Drawings

ENANTIOSELECTIVE PROCESS FOR SYNTHESIS OF (+)- PETROMYROXOL AND ITS DIASTEREOMERS

FIELD OF THE INVENTION

The present invention relates to an enantioselective process for synthesis of (+)-petromyroxol and its Diastereomers from (3aR,5R,6aR)-2,2-dimethyl-5-((R)-oxiran-2-yl)tetrahydrofuro[2,3-d][1,3]dioxole (8).

BACKGROUND AND PRIOR ART

Acetogenins, an important class of compounds containing tetrahydrofuran ring systems, were isolated from Annonaceae plants. They are known to exhibit a wide range of biological activities such as antifeedant, antitumor, immunosuppressive and most significantly pesticidal and pheromonal activities. This interesting biological profile along with varied structural features of the acetogenin family has aroused a lot of research interest in the synthesis of this class of compounds among organic chemists worldwide.

Petromyroxol is a tetrahydrofuran diol from the acetogenin family and one of the vast array of natural compounds that contain a tetrahydrofuran. Petromyroxol was known to have a possible biochemical role in the study of communication among sea lamprey, which are parasitic fish that have been known to cause damage to the fish population especially in the Great lakes area of North America.

The Li and co-workers reported the isolation of a pair of enantiomers from water conditioned with larval Sea Lamprey (*Petromyzonmarinus*) (*Org. Lett.* 2015, 17, 286-289). One of the enantiomers named (+)-petromyroxol (1) showed promising olfactory response in the concentration range of 0.01 to 1 uM. Sea Lamprey is an aggressive predator of trout populations. It is found mainly in the northern Atlantic Ocean and in the western Mediterranean Sea and the main concern is that Sea Lamprey is an invader of the Laurentian Great Lakes which hold nearly 20% of the world's supply of freshwater. Thus there has been a massive research effort on how to control this pest.

Article titled "Enantioselective Synthesis of (+)-Petromyroxol, Enabled by Rhodium-Catalyzed Denitrogenation and Rearrangement of a 1-Sulfonyl-1,2,3-Triazole" by A Boyer published in *J. Org. Chem.*, 2015, 80 (9), pp 4771-4775 reports enantioselective synthesis of (+)-Petromyroxol using by Rhodium-Catalyzed Denitrogenation and Rearrangement of a 1-Sulfonyl-1,2,3-Triazole in 9 steps and 20% overall yield.

Article titled "Total Synthesis of (+)-Petromyroxol, a Marine Natural Product" by S Gahalawat et al. published in *Asian Journal of Organic Chemistry*, 2015, 4 (10), pp 1025-1029 reports an efficient total synthesis of (+)-petromyroxol, by using Sharpless asymmetric dihydroxylation (AD), intramolecular $S_N2$ cyclization and stereoselective Grignard reaction as key steps.

Article titled "Total synthesis of (+)-petromyroxol via tandem α-aminoxylation-allylation and asymmetric dihydroxylation-$S_N2$ cyclization approach" by U Nookaraju et al. published in *RSC Adv.*, 2015,5, pp 63311-63317 reports the total synthesis of (+)-petromyroxol, a tetrahydrofuran (THF)-diol fatty acid, by using a tandem α-aminoxylation-allylation, cross metathesis and tandem asymmetric dihydroxylation-$S_N2$ cyclization as key steps.

The construction of stereochemically defined THF ring has always been a major challenge which is evident from various literature reports. The attractive structural features of petromyroxol along with biological importance and its low abundance drew researcher's attention towards its synthesis. Accordingly, the present invention directed towards an enantioselective process for synthesis of (+)-petromyroxol and its three distereomers by varying the stereochemistry mainly at C5 and/or C6.

OBJECT OF INVENTION

The main objective of the present invention is to provide an enantioselective process for the synthesis of (+)-petromyroxol (1).

Another objective of the present invention is to provide an enantioselective process for the synthesis of 5-epi-(+)-petromyroxol (2).

Yet another objective of the present invention is to provide an enantioselective process for the synthesis of 6-epi-(+)-petromyroxol (3).

Still another objective of the present invention is to provide an enantioselective process for the synthesis of 5,6-bis-epi-(+)-petromyroxol (4).

SUMMARY OF THE INVENTION

Accordingly, the present invention provides an enantioselective process for synthesis of (+)-petromyroxol or its Diastereomers from (3aR,5R,6aR)-2,2-dimethyl-5-((R)-oxiran-2-yl)tetrahydrofuro[2,3-d][1,3]dioxole (8) comprising the steps of:

a) Subjecting epoxide 8 for ring opening using n-BuLi to afford alcohol 9;

b) Benzylating free —OH group of compound of step (a) in the presence of NaH and benzyl bromide in THF to afford benzylether 7;

c) Subjecting benzylether 7 of step (b) for the C-allylation with Allyltrimethylsilane and $BF_3.Et_2O$ in dichloromethane to afford mixture of α and β-C-allylglycosides 10α or 10β;

d) Subjecting allyl glycosides 10α or 10β of step (c) for acetylation to afford corresponding acetates 10α-Ac or 10β-Ac respectively;

e) Subjecting compounds of step (c) for Mitsunobu reaction using p-nitrobenzoic acid and diisopropylazodicarboxylate and triphenyl phosphine in dichloromethane to afford corresponding benzoate;

f) Subjecting benzoate of step (e) or acetates of step (d) for oxidative olefin cleavage using $OsO_4$ and $NaIO_4$ to afford intermediate aldehyde followed by two-carbon Wittig homologation of said aldehyde to afford corresponding unsaturated ester;

g) Hydrogenating unsaturated ester of step (f) to afford saturated ester;

h) Subjecting saturated ester of step (g) to saponification using base in solvent to afford corresponding (+)-petromyroxol (1) or its diastereomers.

In one embodiment, said diastereomers are selected from 5-epi-(+)-petromyroxol (2), 6-epi-(+)-petromyroxol (3), 5,6-bis-epi-(+)-petromyroxol (4).

In preferred embodiment, said acetylation in step (d) is carried out by using acetic anhydride as acylating agent in presence of 4-(N,N,dimethylamino)pyridine as a catalyst.

In another preferred embodiment, said two-carbon Wittig homologation in step (f) is carried out by using ethyl 2-(triphenyl-$\lambda^5$-phosphanylidene) acetate.

In still another preferred embodiment, said hydrogenation in step (g) is carried out under $H_2$ atmosphere in presence of Pearlman catalyst.

In yet another preferred embodiment, said base in step (h) is selected from potassium hydroxide, sodium hydroxide.

In more preferred embodiment, said solvent in step (h) is selected from alcohols such as methanol, ethanol, propanol and butanol.

In another embodiment, said epoxide (8) is (3aR,5R,6aR)-2,2-dimethyl-5-((R)-oxiran-2-yl)tetrahydrofuro[2,3-d][1,3]dioxole.

In yet another embodiment, said alcohol (9) is (S)-1-((3aR,5R,6aR)-2,2-dimethyltetrahydrofuro[2,3-d][1,3]dioxol-5-yl)hexan-1-ol.

In still another embodiment, said benzylether (7) is (3aR,5R,6aR)-5-((S)-1-(benzyloxy)hexyl)-2,2-dimethyltetrahydrofuro[2,3-d][1,3]dioxole.

In yet still another embodiment, said α and β-C-allylglycosides 10α or 10β are (2R,3R,5R)-2-allyl-5 -((S)- 1-(benzyloxy)hexyl)tetrahydrofuran-3 -ol and (2S,3R,5R)-2-allyl-5 -((S)- 1-(benzyloxy)hexyl)tetrahydrofuran-3-ol respectively.

The acetates (10α-Ac) and (10β-Ac) are selected from (2S,3R,5R)-5-((R)-1-(Benzyloxy)hexyl)tetrahydrofuran-3-yl-acetate(10α-Ac, (2R,3R,5R)-5-((R)-1-(Benzylxy)hexyl)tetrahydrofuran-3-yl-acetate (10β-Ac).

The benzoate formed in step (e) is selected from (2S,3S,5R)-5-((R)-1-(Benzyloxy)hexyl)tetrahydrofuran-3-yl-4-nitrobenzoate (6), (2S,3S,5R)-5-((R)-1-(Benzyloxy)hexyl)tetrahydrofuran-3-yl-4-nitrobenzoate (12).

The unsaturated ester formed in step (f) is selected from (2S,3S,5R)-5-((R)-1-(Benzyloxy)hexy)-2-((E)-4-ethoxy-4-oxobut-2-en-1-yl)tetrahydro- furan-3-yl-4-nitrobenzoate (5), (2R,3S,5R)-5-((R)-1-(Benzyloxy)hexy)-2-((E)-4-ethoxy-4-oxobut-2-en-1-yl)tetrahydro-furan-3-yl-4-nitrobenzoate (13), Ethyl (E)-4-((2S,3R,5R)-3-acetoxy-5-((R)-1-(benzyloxy)hexyl)tetrahydrofuran-2-yl)but-2-enoate (15), Ethyl (E)-4-((2R,3R,5R)-3-acetoxy-5-((R)-1-(benzyloxy)hexyl)tetrahydrofuran-2-yl)but-2-enoate (17).

The saturated ester formed in step (g) is selected from (2S,3S,5R)-2-(4-Ethoxy-4-oxobutyl)-5-((R)-1-hydrioxyhehyl)tetrahydrofuran-3-yl-4- aminobenzoate (11), (2R,3S,5R)-2-(4-Ethoxy-4-oxobutyl)-5-((R)-1-hydrioxyhehyl)tetrahydrofuran-3-yl-4-aminobenzoate (14), Ethyl-4-((2S,3R,5R)-3-acetoxy-5-((R)-1-hydroxyhexyl)tetrahydrofuran-2-yl) butan-oate (16), Ethyl-4-((2R,3R,5R)-3-acetoxy-5-((R)-1-hydroxyhexyl)tetrahydrofuran-2-yl)buta-noate (18).

DETAILED DESCRIPTION OF THE INVENTION

The invention will now be described in detail in connection with certain preferred and optional embodiments, so that various aspects thereof may be more fully understood and appreciated.

In the view of the above, the present invention provides an enantioselective process for synthesis of (+)-petromyroxol (1) or its Diastereomers from (3aR,5R,6aR)-2,2-dimethyl-5-((R)-oxiran-2-yl)tetrahydrofuro[2,3-d][1,3]dioxole (8).

In an embodiment, the present invention provides an enantioselective process for synthesis of (+)-petromyroxol (1) or its Diastereomers from (3aR,5R,6aR)-2,2-dimethyl-5-((R)-oxiran-2-yl)tetrahydrofuro[2,3-d][1,3]dioxole (8) comprising the steps of:

a) Subjecting epoxide 8 for ring opening using n-Butyl-lithium (n-BuLi) to afford alcohol 9;

b) Benzylating free —OH group of compound of step (a) in the presence of sodium hydride (NAH) and benzyl bromide in Tetrahydrofuran (THF) to afford benzylether 7;

c) Subjecting benzylether 7 of step (b) for the C-allylation with Allyltrimethylsilane and Boron trifluoride diethyl etherate (BF$_3$.Et$_2$O) in dichloromethane to afford mixture of α and β-C-allylglycosides 10α or 10β;

d) Subjecting allyl glycosides 10α or 10β of step (c) for acetylation to afford corresponding acetates 10α-Ac or 10β-Ac respectively;

e) Subjecting compounds of step (c) for Mitsunobu reaction using p-nitrobenzoic acid and diisopropylazodicarboxylate and triphenyl phosphine in dichloromethane to afford corresponding benzoate;

f) Subjecting benzoate of step (e) or acetates of step (d) for oxidative olefin cleavage using Osmium tetroxide (OsO$_4$) and sodium periodate (NaIO$_4$) to afford intermediate aldehyde followed by two-carbon Wittig homologation of said aldehyde to afford corresponding unsaturated ester;

g) Hydrogenating unsaturated ester of step (f) to afford saturated ester;

h) Subjecting saturated ester of step (g) to saponification using base in solvent to afford corresponding (+)-petromyroxol (1) or its diastereomers.

In one embodiment, said distereomers are selected from 5-epi-(+)-petromyroxol (2), 6-epi-(+)-petromyroxol (3), 5,6-bis-epi-(+)-petromyroxol (4).

In preferred embodiment, acetylation in step (d) is carried out by using acetic anhydride as acylating agent in presence of dimethylaminopyridine as a catalyst.

In another preferred embodiment, said two-carbon Wittig homologation in step (f) is carried out by using ethyl 2-(triphenyl-λ$^5$-phosphanylidene) acetate.

In still another preferred embodiment, hydrogenation in step (g) is carried out under H$_2$ atmosphere and in presence of Pearlman catalyst.

In yet another preferred embodiment, said base in step (h) is selected from potassium hydroxide, sodium hydroxide.

In further preferred embodiment, said solvent in step (h) is selected from alcohols such as methanol, ethanol, propanol and butanol.

In yet another embodiment, said epoxide (8) is (3aR,5R,6aR)-2,2-dimethyl-5-((R)-oxiran-2-yl)tetrahydrofuro[2,3-d][1,3]dioxole.

In still another embodiment, said alcohol (9) is (S)-1-((3aR,5R,6aR)-2,2-dimethyltetrahydrofuro[2,3-d][1,3]dioxol-5-yl)hexan-1-ol In yet still another embodiment, said benzylether (7) is (3aR,5R,6aR)-5-((S)-1-(benzyl oxy)hexyl)-2,2-dimethyltetrahydrofuro [2,3-d][1,3 ]di oxole In further another embodiment, said α and β-C-allylglycosides 10α or 10β are (2R,3R,5R)-2-allyl-5-((S)-1-(benzyloxy)hexyl)tetrahydrofuran-3-ol and (2S,3R,5R)-2-allyl-5-((S)-1-(benzyloxy)hexyl)tetrahydrofuran-3-ol respectively.

The acetates 10α-Ac and 10β-Ac are selected from (2S,3R,5R)-5-((R)-1-(Benzyloxy)hexyl)tetrahydrofuran-3-yl-acetate(10α-Ac), (2R,3R,5R)-5-((R)-1-(Benzylxy)hexyl)tetrahydrofuran-3-yl-acetate (10β-Ac).

The benzoate in step (e) is selected from (2S,3S,5R)-5-((R)-1-(Benzyloxy)hexyl)tetrahydrofuran-3-yl-4-nitrobenzoate (6), (2S,3S,5R)-5-((R)-1-(Benzyloxy)hexyl)tetrahydrofuran-3-yl-4-nitrobenzoate (12).

The unsaturated ester in step (f) is selected from (2S,3S,5R)-5-((R)-1-(Benzyloxy)hexy)-2-((E)-4-ethoxy-4-oxobut-2-en-1-yl)tetrahydro-furan-3-yl-4-nitrobenzoate (5), (2R, 3S,5R)-5-((R)-1-(Benzyloxy)hexy)-2-((E)-4-ethoxy-4-oxobut-2-en-1-yl)tetrahydro-furan-3-yl 4- nitrobenzoate (13), Ethyl (E)-4-((2S,3R,5R)-3-acetoxy-5-((R)-1-(benzyloxy)hexyl)tetrahydrofuran-2-yl) but-2-enoate (15), Ethyl (E)-4-((2R,3R,5R)-3-acetoxy-5-((R)-1-(benzyloxy)hexyl) tetrahydrofuran-2-yl) but-2-enoate (17).

The saturated ester in step (g) is selected from (2S,3S,5R)-2-(4-Ethoxy-4-oxobutyl)-5-((R)-1-hydrioxyhehyl)tetrahydrofuran-3-yl-4- aminobenzoate (11), (2R,3S,5R)-2-(4-Ethoxy-4-oxobutyl)-5-((R)-1-hydrioxyhehyl) tetrahydrofuran-3-yl-4-aminobenzoate (14), Ethyl-4-((2S,3R,5R)-3-acetoxy-5-((R)-1-hydroxyhexyl)tetrahydrofuran-2-yl)butan-oate (16), Ethyl-4-((2R,3R,5R)-3-acetoxy-5-((R)-1-hydroxyhexyl)tetrahydrofuran-2-yl)buta-noate (18).

As depicted in Scheme 1, the epoxide 8 is opened with n-BuLi to introduce the left hand five carbon chain. The free —OH group in the resulting 9 is protected as its benzylether 7 by employing NaH and benzyl bromide in THF. Subsequently, the acetonide 7 is subjected for the C-allylation employing allylTMS and BF$_3$.Et$_2$O in dichloromethane at 0° C. to room temperature, which resulted in a mixture of α- and β-C-allylglycosides 10α/10β (2:7 ratio).

catalyst [20% Pd (OH)$_2$/C] resulted in 11. Finally, the saponification of both the ester groups in 11 is carried out with KOH in methanol to complete the total synthesis of (+)-petromyroxol (1). The spectral data of 1 is comparable with the data reported for the natural product and also the specific rotation confirmed the proposed absolute configuration of (+)-petromyroxol (1). The synthesis of (+)-petromyroxol (1) from 10β is as shown in scheme 2 below;

Scheme 2: Total synthesis of (+)-petromyroxol (1)

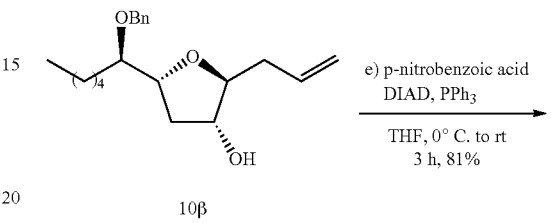

Scheme 1: Synthesis of key allyl C-furanosides 10.

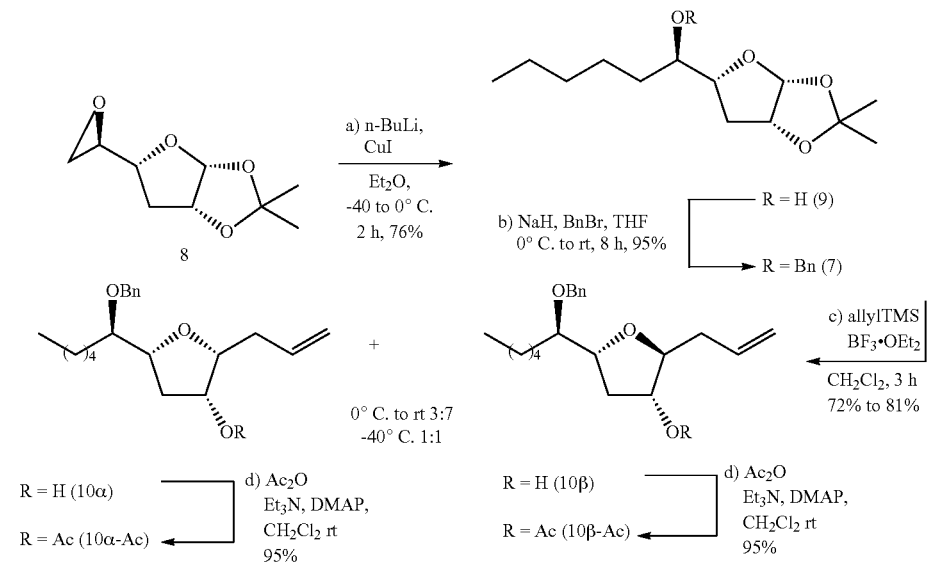

For the purpose of characterization, the ally glycosides 10α/10β are subjected for the acetylation and the corresponding acetates 10α-Ac and 10β-Ac are obtained. The anomeric configuration of these two C-glycosides is established with the help of COSY and NOESY, which revealed that the α-C-furanoside is the minor product. The same reaction has also been examined at −50° C. in the presence of excess Lewis acid and excess allylating agent. The resulting selectivity was seen to drop further to ~1:1.

Further, the compound 10β is subjected for the Mitsunobu reaction employing p-nitrobenzoic acid and diisopropylazodicarboxylate and triphenyl phosphine in dichloromethane to afford the benzoate 6β. The key intermediate 6 having an inverted configuration at the C2. Next, the oxidative olefin cleavage of 6β using OsO$_4$ and NaIO$_4$ resulted in intermediate aldehyde which is immediately subjected for the two-carbon Wittig homologation to afford the unsaturated ester 5. The hydrogenation of 5 using the Pearlman -continued

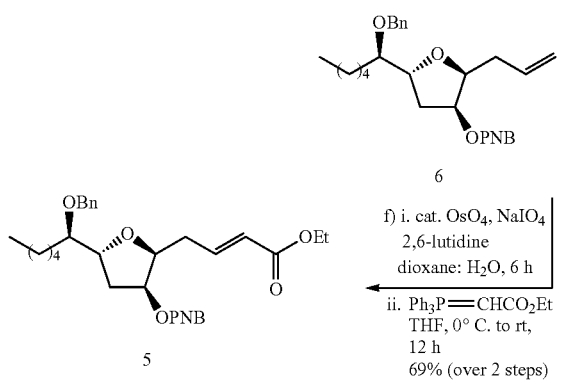

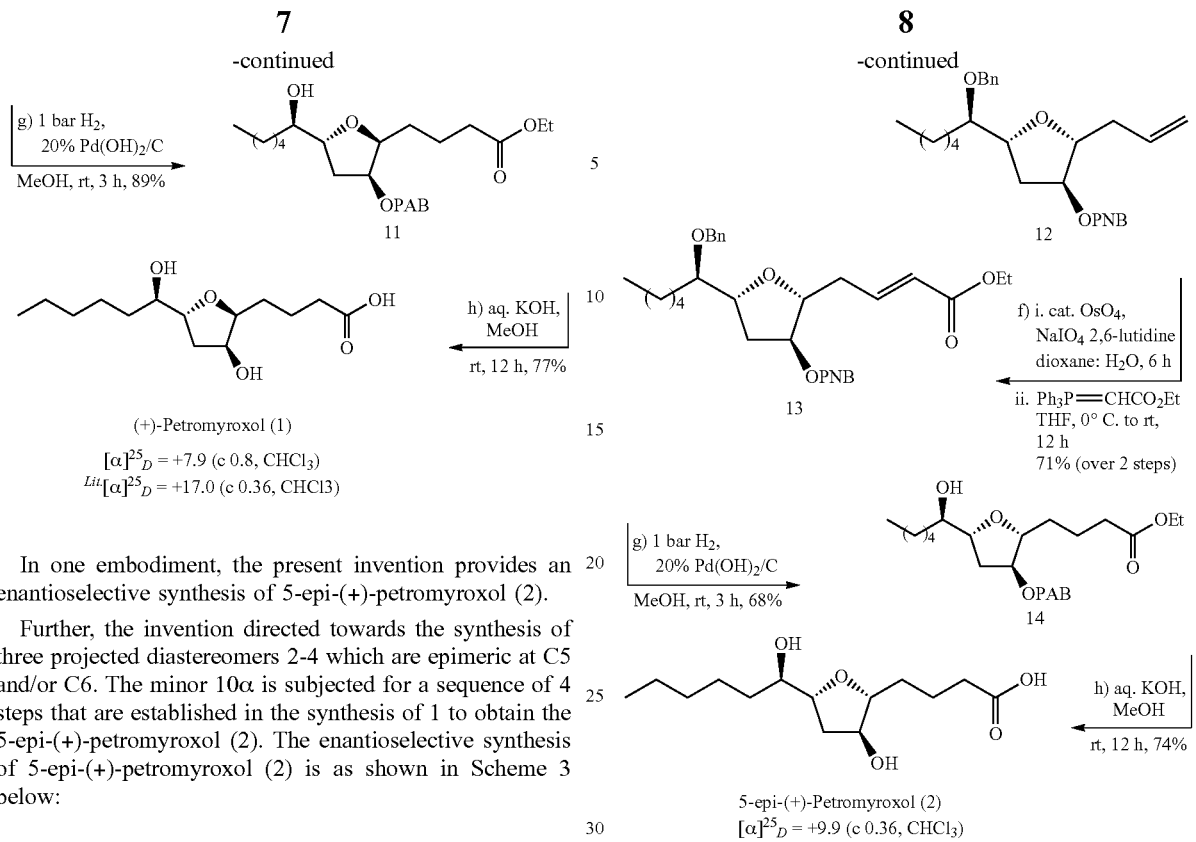

In one embodiment, the present invention provides an enantioselective synthesis of 5-epi-(+)-petromyroxol (2).

Further, the invention directed towards the synthesis of three projected diastereomers 2-4 which are epimeric at C5 and/or C6. The minor 10α is subjected for a sequence of 4 steps that are established in the synthesis of 1 to obtain the 5-epi-(+)-petromyroxol (2). The enantioselective synthesis of 5-epi-(+)-petromyroxol (2) is as shown in Scheme 3 below:

Scheme 3: Synthesis of 5-epi-(+)-petromyroxol (2)

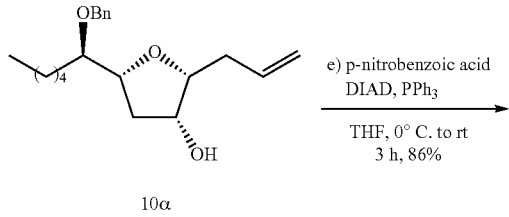

In another embodiment, the present invention provides an enantioselective synthesis of 6-epi-(+)-petromyroxol (3).

The synthesis of 6-epi-(+)-petromyroxol (3) started with the acetate 10β-Ac. As shown in Scheme 4, the treatment of 10β-Ac with cat. $OsO_4$ and $NaIO_4$ followed by the two-carbon Wittig homologation of the resulting intermediate aldehyde give the unsaturated ester 16. The hydrogenation of 15 under established conditions and the saponification of the resulting 16 employing KOH in methanol provided the projected 6-epi-(+)-petromyroxol (3). The synthesis of 6-epi-(+)-petromyroxol (3) is as shown in scheme 4 below:

Scheme 4: Synthesis of 6-epi-(+)-petromyroxol (3)

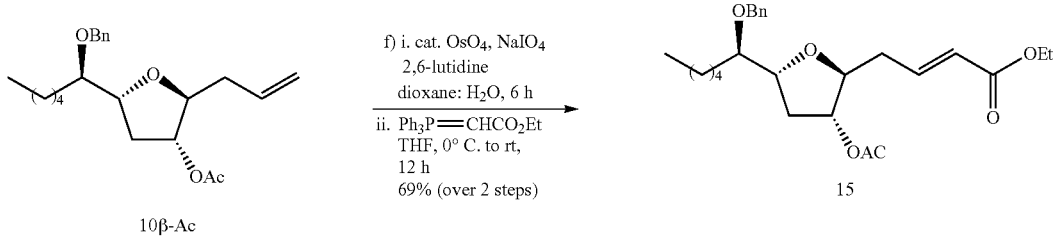

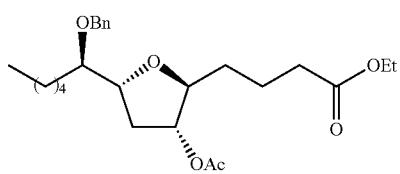

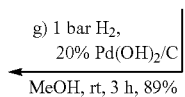

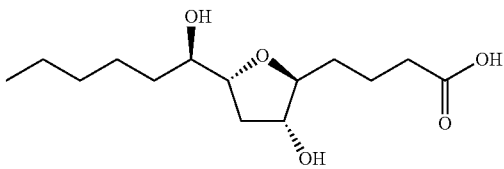

6-epi-(+)-Petromyroxol (3)
$[\alpha]^{25}_D = -27.6$ (c 0.6, CHCl$_3$)

In still another embodiment, the present invention provides an enantioselective synthesis of 5,6-bis-epi-(+)-petromyroxol (4).

Similarly, as shown in above scheme 4 when the minor 10α-Ac is subjected for a sequence of 3 steps that are established in the synthesis of 3 which afford 5,6-bis-epi-(+)-petromyroxol (4). The synthesis of 5,6-bis-epi-(+)-petromyroxol is as shown in scheme 5 below:

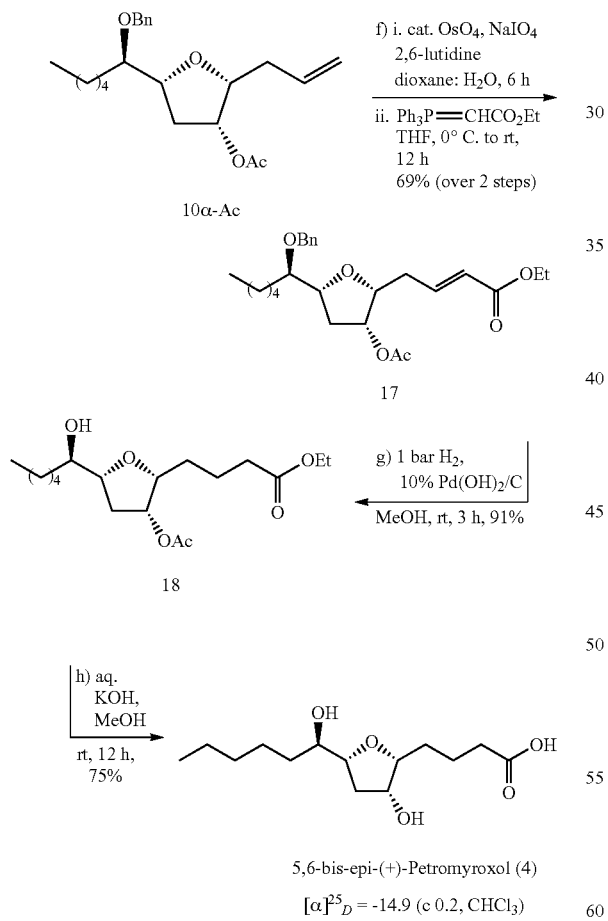

EXAMPLES

Example 1

Synthesis of (S)-1-((3aR,5R,6aR)-2,2-dimethyltetrahydrofuro[2,3-d][1,3]dioxol-5-yl)hexan-1-ol (9)

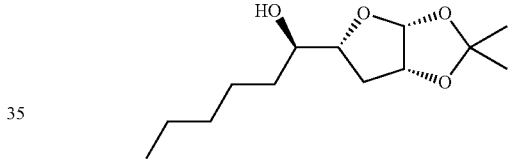

At −10° C., a suspension of CuI (1.53 g, 4.03 mmol) in dry Et$_2$O (50 mL) was treated with n-BuLi (10.1 mL, 16.1 mmol) and contents were stirred for 15 min. To this, a solution of epoxide 8 (1 g, 5.4 mmol) in Et$_2$O (5 mL) was introduced and mixture was stirred for 3 hours at 0° C. After completion of the reaction, the reaction mixture was quenched with saturated NH$_4$Cl (50 mL) and the layers are separated. The aqueous layer was extracted with Et$_2$O (2×30 mL) and the combined organic layer was washed with brine, dried (Na$_2$SO$_4$) and concentrated. Purification of the residue was carried out by silica gel column chromatography (20→25% EtOAc in petroleum ether) to afford alcohol 9 (995 mg, 76%) as colorless oil. R$_f$ 0.4 (30% EtOAc in petroleum ether); $[\alpha]_D^{25}$: −1.4 (c 2.2, CHCl$_3$); $^1$H NMR (CDCl$_3$, 200 M Hz): δ0.89 (t, J=6.4 Hz, 3H), 1.31 (s, 3H), 1.28-1.52 (m, 8H), 1.55 (s, 3H), 1.98 (ddd, J=1.2, 3.2, 14.3 Hz, 1H), 2.11-2.26 (m, 1H), 2.72 (d, J=1.6 Hz, 1H), 3.76 (bt, J=3.76 Hz, 1H), 3.95 (td, J=3.2, 8.2 Hz, 1H), 4.76 (ddd, J=1.1, 3.9, 7.3 Hz, 1H), 5.81 (d, J=4.0 Hz, 1H); $^{13}$C NMR (CDCl$_3$, 50 M Hz): δ14.0 (q), 22.5 (t), 25.3 (t), 25.9 (q), 26.9 (q), 31.8 (t), 33.1 (t), 33.6 (t),72.7 (d), 80.7 (d), 84.7 (d), 106.1 (d), 112.3(s), ppm; HRMS (ESI+) calculated for C$_{13}$H$_{24}$O$_4$Na 267.1675, found 267.1572.

The following examples, which include preferred embodiments, will serve to illustrate the practice of this invention, it being understood that the particulars shown are by way of example and for purpose of illustrative discussion of preferred embodiments of the invention.

Example 2

Synthesis of (3aR,5R,6aR)-5-((S)-1-(benzyloxy)hexyl)-2,2-dimethyltetrahydrofuro[2,3-d][1,3]dioxole (7)

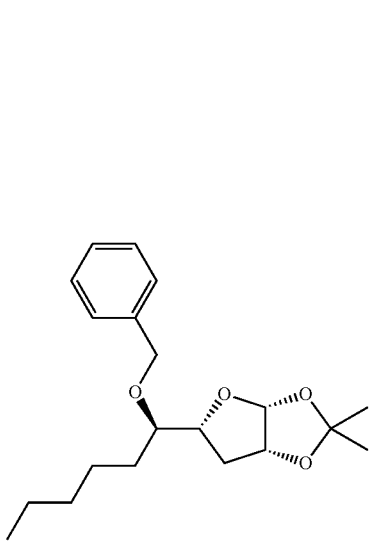 [SMILES: CCCCC[C@@H](OCc1ccccc1)[C@H]1C[C@H]2OC(C)(C)O[C@H]2O1]

To a cooled solution of the alcohol 9 (900 mg, 2.86 mmol) in anhydrous DMF (25 mL), NaH (60%, 220 mg, 5.53 mmol) was added slowly and stirred for 10 min, to this benzyl bromide (0.6 mL, 4.8 mmol) was added drop wise and stirring was continued at rt for 6 h. The reaction mixture was partitioned between water and EtOAc and the aqueous layer was extracted with EtOAc (2×20 mL). The combined organic layer was dried (Na$_2$SO$_4$) and concentrated under reduced pressure. Purification of the residue by silica gel column chromatography (8→10% EtOAc in petroleum ether) gave 7 (1.12 g, 95%) as colorless syrup. R$_f$ 0.6 (20% EtOAc in petroleum ether); $[\alpha]_D^{25}$: −2.8 (c3.9, CHCl$_3$); $^1$H NMR (CDCl$_3$, 400 M Hz): δ 0.90 (t, J=6.9 Hz, 3H), 1.26-1.31 (m, 4H), 1.36 (s, 3H), 1.40-1.52 (m, 4H), 1.59 (s, 3H), 1.98 (ddd, J=1.8, 5.0, 14.2 Hz, 1H), 2.18 (ddd, J=6.4, 7.8, 14.2 Hz, 1H), 3.66 (td, J=2.7, 8.2 Hz, 1H), 4.13 (td, J=5.0, 8.2 Hz, 1H), 4.65 (d, J=11.4 Hz, 1H), 4.76 (ddd, J=1.8, 4.1, 6.4 Hz, 1H), 4.97 (d, J=11.4 Hz, 1H), 5.81 (d, J=4.1 Hz, 1H), 7.25-7.43 (m, 5H); $^{13}$C NMR (CDCl$_3$, 50 M Hz): δ14.0 (q), 22.5 (t), 25.0 (t), 26.3 (q), 27.3 (q), 31.6 (t), 31.8 (t), 34.2 (t), 73.5 (t), 80.6 (d), 80.9 (d), 84.1 (d), 106.2 (d), 112.4 (s),127.3 (d), 128.0 (d, 2c), 128.1 (d, 2c), 139.2 (S) ppm; HRMS (ESI+) calculated for C$_{20}$H$_{30}$O$_4$Na 357.2144, found 357.2041.

Example 3

Synthesis of (2R,3R,5R)-2-allyl-5-((S)-1-(benzyloxy)hexyl)tetrahydrofuran-3-ol (10α) and (2S,3R,5R)-2-allyl-5-((S)-1-(benzyloxy)hexyl)tetrahydrofuran-3-ol (10β)

To an ice-cold solution of 7 (1 g, 3.0 mmol) in dry CH$_2$Cl$_2$ (50 mL), allyl trimethylsilane (2.38 mL, 14.9 mmol) was added and after 15 min of stirring, BF$_3$.Et$_2$O (947 mmL, 8.97 mmol) was slowly added to it and then the contents were stirred at room temperature for 2 h. The reaction mixture was quenched with saturated NaHCO$_3$ (50 mL) and the organic layer was separated and the aqueous layer was extracted with CH$_2$Cl$_2$. The combined organic layer was washed with water (50 mL), dried (Na$_2$SO$_4$), and concentrated under vacuum. The purification of residue by silica gel chromatography (10→16% EtOAc in petroleum ether) gave α-C-glycoside 10α (542 mg, 57%) and β-C-glycoside10β (232 mg, 24%).

Characterization data of 10α: Colorless gum; R$_f$ 0.5 (30% EtOAc in petroleum ether); $[\alpha]_D^{25}$: −19.1 (c0.8, CHCl$_3$); $^1$H NMR (CDCl$_3$, 500 M Hz): δ 0.91 (t, J=6.7 Hz, 3H), 1.30-1.49 (m, 6H), 1.74-1.78 (m, 3H), 2.27 (ddd, J=5.9, 9.8, 14.9 Hz, 1H), 2.40-2.44 (m, 2H), 3.26 (ddd, J=2.1, 5.8, 8.3 Hz, 1H), 3.59 (td, J=2.4, 6.7 Hz, 1H), 3.75 (bs, 1H), 3.98 (ddd, J=2.5, 5.2, 10.9 Hz, 1H), 4.14 (dt, J=2.7, 10.1 Hz, 1H), 4.49 (d, J=11.3 Hz, 1H), 4.72 (d, J=11.3 Hz, 1H), 5.04 (dd, J=2.0, 8.6 Hz, 1H), 5.13 (dd, J=1.8, 17.10 Hz, 1H), 5.86 (ddt, J=7.1, 10.2, 14.1 Hz, 1H), 7.30-7.37 (m, 5H); $^{13}$C NMR (CDCl$_3$, 100 M Hz): δ14.0 (q), 22.6 (t), 25.6 (t), 29.7 (t), 32.0 (t), 33.5 (t), 37.6 (t), 71.3 (d), 72.2 (t), 77.5 (d), 80.3 (d), 83.5 (d), 116.7 (t), 128.1 (d), 128.5 (d, 2C), 128.6 (d, 2C), 135.2 (d), 137.3 (s) ppm; HRMS (ESI+) calcd for C$_{20}$H$_{30}$O$_3$Na 341.2195 found 341.2092.

Characterization data of 10β: Colourless gum; R$_f$ 0.4 (20% EtOAc in petroleum ether); [α]$_D^{25}$: −24.3 (c1.7, CHCl$_3$); $^1$H NMR (CDCl$_3$, 400 M Hz): δ0.91 (t, J=6.6 Hz, 3H), 1.27-1.45 (m, 6H), 1.72-1.76 (m, 3H), 2.07-2.25 (m, 2H), 2.32 (ddd, J=6.1, 9.3, 15.4 Hz, 1H), 3.28 (td, J=2.4, 6.6 Hz, 1H), 3.81 (d, J=10.3 Hz, 1H), 3.97 (bt, J=6.4 Hz, 2H), 4.21 (dt, J=3.2, 9.3 Hz, 1H), 4.52 (d, J=11.2 Hz, 1H), 4.72 (d, J=11.5 Hz, 1H), 5.05 (dd, J=1.8, 7.7 Hz, 1H), 5.09 (dd, J=1.6, 14.0 Hz, 1H), 5.81 (ddt, J=6.9, 10.2, 13.9 Hz 1H), 7.30-7.37 (m, 5H); $^{13}$C NMR (CDCl$_3$, 100 M Hz): δ14.0 (q), 22.6 (t), 25.5 (t), 29.7 (t), 32.0 (t), 36.3 (t), 37.8 (t), 72.1 (t), 74.6 (d), 78.1 (d), 80.8 (d), 86.6 (d), 117.1 (t), 128.1 (d), 128.5 (d, 4C), 134.4 (d), 137.4 (s) ppm; HRMS (ESI+) calculated for C$_{20}$H$_{30}$O$_3$Na 341.2195 found 341.2092.

Example 4

Synthesis of (2S,3R,5R)-5-((R)-1-(Benzyloxy)hexyl)tetrahydrofuran-3-yl-acetate(10α-Ac):

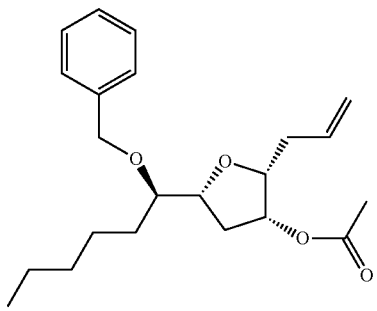 [SMILES: C=CC[C@H]1O[C@@H]([C@@H](CCCCC)OCc2ccccc2)C[C@H]1OC(C)=O]

To a solution of alcohol 10α (500 mg, 1.57 mmol), Et$_3$N (0.65 mL, 4.7 mmol) and DMAP (2 mg) in CH$_2$Cl$_2$ (20 mL) at 0° C. was added acetic anhydride (0.3 mL, 3.14 mmol) and stirred for 2 h. The reaction mixture was diluted with CH$_2$Cl$_2$ (20 mL) and washed with brine (20 mL) dried (Na$_2$SO$_4$) and concentrated under reduced pressure. The purification of residue by silica gel chromatography (8→12% EtOAc in petroleum ether) gave acetate 10α-Ac (75 mg, 91%) as colorless syrup. R$_f$ 0.7 (20% EtOAc in petroleum ether); [α]$_D^{25}$: −1.5 (c1.1, CHCl$_3$); $^1$H NMR (CDCl$_3$, 400 M Hz): δ 0.89 (t, J=6.8 Hz, 3H), 1.27-1.49 (m, 8H), 1.71 (ddd, J=2.7, 7.6, 14.2 Hz, 1H), 2.06 (s, 3H), 2.33-2.42 (m, 2H), 2.44-2.51 (m, 1H), 3.43-3.47 (m, 1H), 3.80 (ddd, J=4.4, 6.4, 10.5 Hz, 1H), 3.96 (bq, J=7.3 Hz, 1H), 4.65 (d, J=11.5 Hz, 1H), 4.78 (d, J=11.7 Hz, 1H), 5.07 (dd, J=1.7, 11.6 Hz, 1H), 5.12 (dd, J=1.7, 17.1 Hz, 1H), 5.24 (ddd, J=2.7, 4.2, 7.0 Hz, 1H), 5.86 (ddt, J=7.0, 10.2, 14.0 Hz 1H), 7.27-7.39 (m, 5H); $^{13}$C NMR (CDCl$_3$, 100 M Hz): δ14.0 (q), 21.0 (q), 22.6 (t), 25.2 (t), 30.9 (t), 31.9 (t), 33.7 (t), 35.8 (t), 73.0 (t), 74.2 (d),80.4 (d), 80.8 (d, 2C), 116.9 (t), 127.4 (d),128.0 (d, 2C), 128.2 (d, 2C), 134.5 (d), 139.1 (s), 170.5 (s), ppm; HRMS (ESI+) calculated for C$_{22}$H$_{32}$O$_4$Na 383.2301 found 383.2198.

Example 5

Synthesis of (2R,3R,5R)-5-((R)-1-(Benzylxy)hexyl)tetrahydrofuran-3-yl-acetate (10β-Ac)

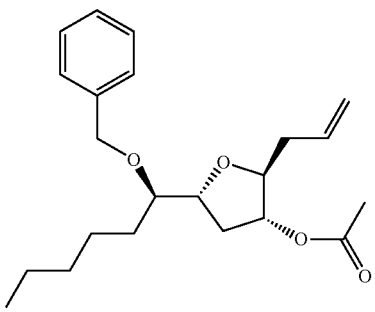 [SMILES: C=CC[C@@H]1O[C@@H]([C@@H](CCCCC)OCc2ccccc2)C[C@H]1OC(C)=O]

To a solution of alcohol 10β (200 mg, 0.63 mmol), Et$_3$N (0.26 mL, 1.88 mmol) and DMAP (2 mg) in CH$_2$Cl$_2$ (15 mL) at 0° C. was added acetic anhydride (118 mmL, 1.26 mmol) and stirred for 2 h. The reaction mixture was diluted with CH$_2$Cl$_2$ (10 mL) and washed with brine (20 mL), dried (Na$_2$SO$_4$) and concentrated under vacuum. The purification of residue by silica gel chromatography (6→8% EtOAc in petroleum ether) to gave acetate 10β-Ac (214 mg, 95%) as colorless syrup. R$_f$ 0.8 (20% EtOAc in petroleum ether); [α]$_D^{25}$: −9.5 (c1.9, CHCl$_3$); $^1$H NMR (CDCl$_3$, 400 M Hz): δ 0.90 (t, J=7.0 Hz, 3H), 1.26-1.50 (m, 8H), 1.81 (ddd, J=5.1, 7.2, 13.5 Hz, 1H), 2.05 (s, 3H), 2.34 (bt, J=6.7 Hz, 2H), 2.43 (dt, J=7.3, 13.0 Hz, 1H), 3.45 (dt, J=4.9, 6.3 Hz, 1H), 4.08 (dt, J=3.9, 6.4 Hz, 1H), 4.17 (bq, J=7.1 Hz, 1H), 4.65 (d, J=11.7 Hz, 1H), 4.76 (d, J=11.5 Hz, 1H), 4.97 (dt, J=4.5, 7.1 Hz, 1H), 5.09 (dd, J=1.6, 10.8 Hz, 1H), 5.14 (dd, J=1.7, 18.0 Hz, 1H), 5.86 (ddt, J=7.0, 7.2, 14.0 Hz, 1H), 7.28-7.40 (m, 5H); $^{13}$C NMR (CDCl$_3$, 100 M Hz): δ14.0 (q), 21.1 (q), 22.6 (t), 25.2 (t), 30.7 (t), 31.9 (t), 34.1 (t), 37.1 (t), 72.9 (t), 77.4 (d), 80.0 (d), 80.6 (d), 81.9 (d), 117.5 (t), 127.4 (d), 127.9 (d, 2C), 128.2 (d, 2c), 133.9 (d), 139 (s), 170.7 (s), ppm; HRMS (ESI+) calculated for C$_{22}$H$_{32}$O$_4$Na 383.2301 found 383.2198.

Example 6

Synthesis of (2S,3S,5R)-5-((R)-1-(Benzyloxy)hexyl)tetrahydrofuran-3-yl-4-nitrobenzoate (6)

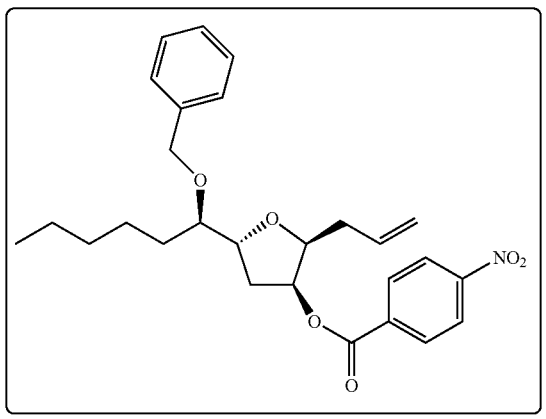 [SMILES: C=CC[C@@H]1O[C@@H]([C@@H](CCCCC)OCc2ccccc2)C[C@@H]1OC(=O)c1ccc([N+](=O)[O-])cc1]

To a solution of alcohol 10β (200 mg, 6.3 mmol), p-nitrobenzoic acid (315 mg, 1.88 mmol), and TPP (330 mg, 1.26 mmol) in THF (15 mL) at 0° C. was treated with diisopropylazodicarboxylate (0.24 mL, 1.26 mmol) and the contents were stirred at 0° C. for 1 h and then at rt for 5 h. After completion of the reaction, the reaction mixture was concentrated and the resulting crude material is dissolved in EtOAc (60 mL), washed with the aqueous NaHCO$_3$ (30 mL), water (50 mL), dried (Na$_2$SO$_4$) and concentrated in vacuum. The purification of residue by silica gel column chromatography (10→12% EtOAc in petroleum ether) gave ester 6 (238 mg, 81%) as yellow oil. R$_f$ 0.6 (20% EtOAc in petroleum ether); $[\alpha]_D^{25}$+11.7 (c0.9, CHCl$_3$); $^1$H NMR (CDCl$_3$, 400 M Hz): δ 0.89 (t, J=6.8 Hz, 3H), 1.28-1.56 (m, 8H), 2.12-2.24 (m, 2H), 2.39-2.57 (m, 2H), 3.36 (ddd, J=5.4, 5.4, 10.6 Hz, 1H), 4.19 (td, J=3.2 , 7.0 Hz, 1H), 4.38 (ddd, J=5.1, 6.7, 12.2 Hz, 1H), 4.69 (d, J=2.0 Hz, 2H), 5.05 (dd, J=1.6, 9.6 Hz, 1H), 5.08 (dd, J=1.6, 17.0 Hz, 1H), 5.59 (dd, J=3.2, 3.2 Hz, 1H), 5.82 (ddt, J=7.0, 10.2, 13.8 Hz, 1H), 7.28-7.38 (m, 5H), 8.24 (d, J=8.8 Hz, 2H), 8.32 (d, J=8.8 Hz, 2H); $^{13}$C NMR (CDCl$_3$, 100 M Hz): δ14.0 (q), 22.6 (t), 25.3 (t), 30.6 (t), 32.0 (t), 34.1 (t), 35.5 (t), 72.9 (t), 76.8 (d), 79.8 (d), 80.7 (d), 80.9 (d), 117.3 (t), 123.6 (d, 2C), 127.6 (d,), 127.9 (d, 2C), 128.3 (d, 2C), 130.8 (d, 2C), 134.0 (d), 135.4 (s), 138.8 (s), 150.7 (s), 164.0 (s) ppm; HRMS (ESI+) calculated for C$_{27}$H$_{33}$NO$_6$Na 490.2308, found 490. 2205.

Example 7

Synthesis of (2S,3S,5R)-5-((R)-1-(Benzyloxy) hexy)-2-((E)-4-ethoxy-4-oxobut-2-en-1-yl)tetra-hydro-furan-3-yl-4-nitrobenzoate (5)

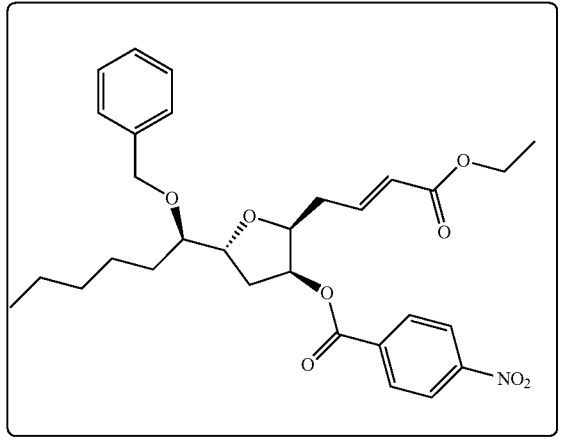 [SMILES: CCCCC[C@@H](OCc1ccccc1)[C@H]1C[C@H](OC(=O)c2ccc([N+](=O)[O-])cc2)[C@H](C/C=C/C(=O)OCC)O1]

To a cooled solution of alkene 6 (200 mg, 0.427 mmol) in dioxane-water (3:1, 8 mL) were added 2,6-lutidine (0.1 mL, 0.86 mmol), OsO$_4$ (2.17 mg, 0.008 mmol), and NaIO$_4$ (366 mg, 1.71 mmol) and the contents were stirred at rt for 6 h. After the reaction was complete, water (20 mL) and CH$_2$Cl$_2$ (30 mL) were added. The organic layer was separated, and the water layer was extracted by CH$_2$Cl$_2$ (2×10 mL) and the combined organic layer was dried (Na$_2$SO$_4$) and concentrated under vacuum to get crude aldehyde. To a solution of above crude aldehyde in THF (15 mL) was cooled to 0° C. and treated with ethyl 2-(triphenyl-λ$^5$-phosphanylidene) acetate (440 mg, 1.32 mmol) and the contents were stirred at rt for 10 h. The reaction mixture was diluted with water (40 mL) and extracted with EtOAc (2×30 mL), dried (Na$_2$SO$_4$) and concentrate under vacuum. The purification of residue by silica gel column chromatography (18→20% EtOAc in petroleum ether) gave ester 5 (160 mg, 69% over 2 steps) as a white solid.

R$_f$ 0.5 (30% EtOAc in petroleum ether); MP: 91° C.; $[\alpha]_D^{25}$+16.0 (c4.1, CHCl$_3$); $^1$H NMR (CDCl$_3$, 500 M Hz): δ0.88 (t, J=6.7 Hz, 3H), 1.23 (t, J=7.3 Hz, 3H), 1.28-1.58 (m, 8H), 2.16 (dd, J=6.7, 13.7 Hz, 1H), 2.22 (ddd, J=5.2, 9.2, 14.0 Hz, 1H), 2.52-2.63 (m, 2H), 3.35 (ddd, J=5.2, 5.2, 10.5 Hz, 1H), 4.13 (q, J=7.0 Hz, 2H), 4.25 (ddd, J=3.3, 5.8, 8.9 Hz, 1H), 4.38 (ddd, J=5.0, 6.4, 11.8 Hz, 1H), 4.66 (s, 2H), 5.59 (dd, J=3.4, 3.4 Hz, 1H), 5.86 (d, J=15.9 Hz, 1H), 6.98 (dt, J=7.0, 15.6 Hz, 1H), 7.26-7.36 (m, 5H), 8.20 (d, J=8.8 Hz, 2H), 8.29 (d, J=8.8 Hz, 2H) ; $^{13}$C NMR (CDCl$_3$, 125 M Hz): δ14.0 (q), 14.1 (q), 22.5 (t), 25.2 (t), 30.6 (t), 31.9 (t), 32.5 (t), 35.4 (t), 60.2 (t), 72.8 (t), 76.9 (d), 79.4 (d), 79.8 (d), 80.8 (d), 123.4 (d), 123.6 (d, 2C), 127.5 (d), 127.9 (d, 2C), 128.3 (d, 2C),130.7 (d, 2C) 135.1 (s), 138.6 (s), 144.1 (d), 150.7 (s), 163.9 (s), 166.1 (s) ppm; HRMS (ESI+) calculated for C$_{30}$H$_{37}$NO$_8$Na 562.2519, found 562.2408.

Example 8

Synthesis of (2S,3S,5R)-2-(4-Ethoxy-4-oxobutyl)-5-((R)-1-hydrioxyhehyl)tetrahydrofuran-3-yl-4-aminobenzoate (11)

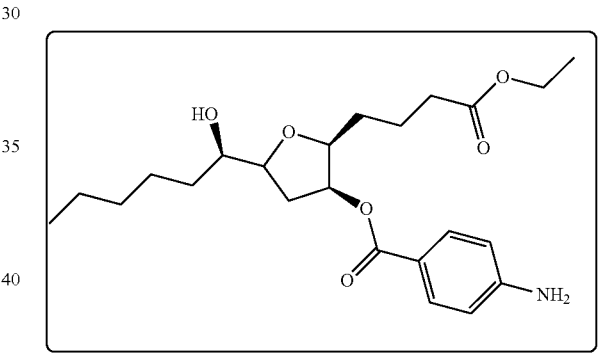

To a solution of ester 5 (150 mg, 0.27 mmol) in MeOH (10 mL) was added 20% Pd(OH)$_2$/C (13 mg) and the reaction mixture is stirred at rt under H$_2$ atmosphere (balloon) for 3 h. After completion of the reaction, reaction mixture is filtered through a pad of Celite and the Celite pad was washed thoroughly with EtOAc. Combined filtrate was evaporated under vacuum. The purification of residue by silica gel column chromatography (25→30% EtOAc in petroleum ether) gave ester 11 (104 mg, 89%) as colourless oil. R$_f$ 0.5 (40% EtOAc in petroleum ether); $[\alpha]_D^{25}$+12.2 (c1.5, CHCl$_3$) ; $^1$H NMR (CDCl$_3$, 400 M Hz): δ 0.89 (t, J=6.4 Hz, 3H), 1.22 (t, J=7.0 Hz, 3H), 1.28-1.53 (m, 8H), 1.64-1.82 (m, 4H), 2.03-2.10 (m, 2H), 2.15 (dd, J=6.6, 13.9 Hz, 1H), 2.32 (t, J=6.6 Hz, 2H), 3.43 (dt, J=7.6, 10.8 Hz, 1H), 4.09 (q, J=7.0, 14.2 Hz, 2H), 4.02-4.06 (m, 2H), 4.09 (q, J=7.2 Hz, 2H), 5.51 (dd, J=3.5, 3.5 Hz, 1H), 6.65 (d, J=8.6 Hz, 2H), 7.85 (d, J=8.6 Hz, 2H); $^{13}$C NMR (CDCl$_3$, 100 M Hz): δ14.0 (q), 14.2 (q), 21.8 (t), 22.6 (t), 25.2 (t), 28.9 (t), 31.8 (t), 33.3 (t), 34.2 (t), 35.7 (t), 60.3 (t), 74.0 (d), 75.4 (d), 80.8 (d), 81.2 (d), 113.8 (d, 2C), 119.3 (s), 131.7 (d, 2C), 151.1 (s), 165.8 (s), 173.4 (s) ppm; HRMS (ESI+) calculated for C$_{23}$H$_{35}$NO$_6$Na 444.2464, found 444.2361.

Example 9

Synthesis of (+)-Petromyroxol (1):

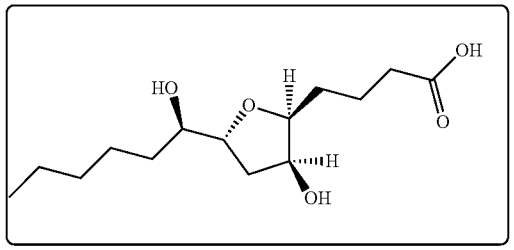 [SMILES: CCCCC[C@@H](O)[C@H]1C[C@H](O)[C@H](CCCC(=O)O)O1]

To a solution of ester 11 (70 mg, 0.11 mmol) in MeOH (10 mL) was added KOH (13 mg, 0.24 mmol) and the reaction mixture is stirred for 10 hours at rt. After completion of the reaction, solvent is removed under vacuum and the crude material is diluted with $CH_2Cl_2$ and water, then acidified with dilute HCl and the aqueous layer is extracted with $CH_2Cl_2$ (2×20 mL) the combined organic layer was dried ($Na_2SO_4$) and concentrated in vacuum, The purification of residue by silica gel column chromatography (100% EtOAc) resulted in (+)-Petromyroxol (1) (35 mg, 77%) as colourless oil. $R_f$ 0.2 (100% AcOEt); $[\alpha]_D^{25}$+7.9 (c0.8, $CHCl_3$)-$^{Lit}$ $[\alpha]_D^{25}$17.0 (c 0.36, $CHCl_3$); $^1$H NMR ($CDCl_3$, 500 M Hz): δ 0.89 (t, J=7.0 Hz, 3H), 1.28-1.31 (m, 2H), 1.32-1.35 (m, 2H), 1.36-1.40 (m, 2H), 1.41-56 (m, 2H), 1.63-1.80 (m, 4H), 1.89 (ddd, J=4.6, 9.2, 13.4 Hz, 1H), 2.03 (dd, J=6.7, 13.4 Hz, 1H), 2.43 (m, 2H), 3.40 (ddd, J=4.1, 6.3, 8.9 Hz, 1H), 3.80 (ddd, J=2.9, 6.9, 8.9 Hz, 1H), 4.06 (ddd, J=4.5, 6.4, 12.7 Hz, 1H), 4.30 (dd, J=2.8, 5.2 Hz, 1H); $^{13}$C NMR ($CDCl_3$, 125 M Hz): δ14.2 (q), 21.4 (t), 22.7 (t), 25.4 (t), 28.3 (t), 32.0 (t), 33.2 (t), 33.8 (t), 37.7 (t), 73.4 (d), 74.3 (d), 80.7 (d), 82.5 (d), 178.0 (s) ppm; HRMS (ESI+) calculated for $C_{14}H_{26}O_5Na$ 297.1780, found 297.1677.

Example 10

Synthesis of (2S,3S,5R)-5-((R)-1-(Benzyloxy)hexyl)tetrahydrofuran-3-yl-4-nitrobenzoate (12)

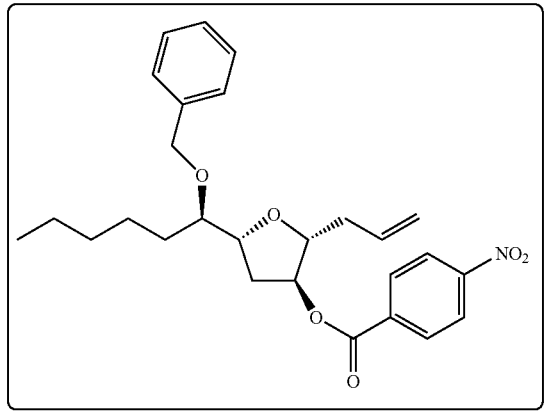 [SMILES: C=CC[C@H]1O[C@@H]([C@@H](CCCCC)OCc2ccccc2)C[C@@H]1OC(=O)c1ccc([N+](=O)[O-])cc1]

The same procedure as in the preparation of 6 was used with the alcohol 10α (165 mg, 0.5 mmol), affording 12 (209 mg, 86%) as a yellow oil. $R_f$ 0.6 (20% EtOAc in petroleum ether); $[\alpha]_D^{25}$+19.8 (c2.3, $CHCl_3$). $^1$H NMR ($CDCl_3$, 400 M Hz): δ 0.89 (t, J=6.9 Hz, 3H), 1.24-1.56 (m, 8H), 2.05 (q, J=4.1 Hz, 2H), 2.45 (t, J=6.4 Hz, 2H), 3.41 (ddd, J=3.6, 4.1, 9.9 Hz, 1H), 4.18 (td, J=2.3, 6.4 Hz, 1H), 4.26 (dt, J=6.4, 14.1 Hz, 1H), 4.67 (d, J=11.4 Hz, 1H), 4.78 (d, J=11.4 Hz, 1H), 5.13 (dd, J=1.7, 10.0 Hz, 1H), 5.18 (dd, J=1.7, 17.0 Hz, 1H), 5.26 (ddd, J=2.0, 2.7, 5.9 Hz, 1H), 5.89 (ddt, J=6.9, 10.2, 14.0 Hz, 1H), 7.29-7.41 (m, 5H), 8.19-8.22 (m, 2H), 8.29-8.33 (m, 2H); $^{13}$C NMR ($CDCl_3$, 50 M Hz): δ14.0 (q), 22.6 (t), 25.2 (t), 31.1 (t), 31.9 (t), 34.6 (t), 38.5 (t), 73.0 (t), 79.3 (d), 80.9 (d), 81.6 (d), 83.5 (d), 117.8 (t), 123.6 (d, 2C), 127.5 (d), 128.0 (d, 2C), 128.2 (d, 2C), 130.7 (d, 2C), 133.7 (d), 135.3 (s), 138.9 (s), 150.6 (s), 164.2 (s)ppm; HRMS (ESI+) calculated for $C_{27}H_{33}NO_6Na$ 490.2308, found 490.2193.

Example 11

Synthesis of (2R,3S,5R)-5-((R)-1-(Benzyloxy)hexy)-2-((E)-4-ethoxy-4-oxobut-2-en-1-yl)tetrahydro-furan-3-yl-4-nitrobenzoate (13)

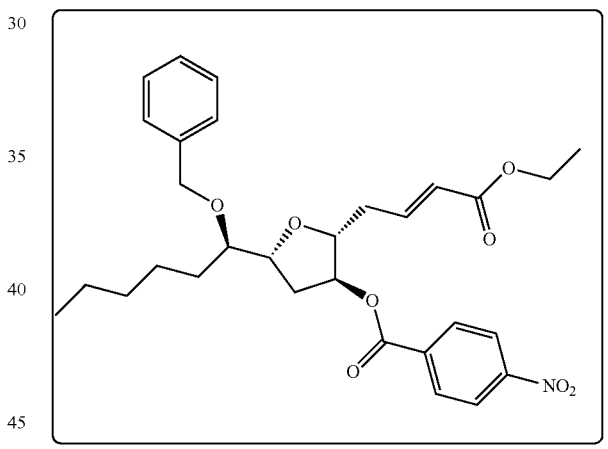

The same procedure as in the preparation of 5 was used with the alkene 12 (200 mg, 0.43 mmol), gave ester 13 (136 mg, 71% over 2 steps) as a white solid. $R_f$ 0.6 (30% EtOAc in petroleum ether), MP: 83° C.; $[\alpha]_D^{25}$+24.9 (c2.9, $CHCl_3$) ; $^1$H NMR ($CDCl_3$, 200 M Hz): δ 0.89 (t, J=6.6 Hz, 3H), 1.27 (t, J=7.2, Hz, 3H), 1.24-1.53 (m, 8H), 2.08 (dd, J=4.0, 7.8 Hz, 2H), 2.48-2.72 (m, 2H), 3.39 (dt, J=4.9, 10.9 Hz, 1H), 4.18 (q, J=7.0 Hz, 2H), 4.26 (ddd, J=5.9, 8.1, 14.5 Hz, 2H), 4.65 (d, J=11.3 Hz, 1H), 4.71 (d, J=11.6 Hz, 1H), 5.21 (ddd, J=2.5, 4.2, 6.7 Hz, 1H), 5.97 (d, J=15.7 Hz, 1H), 7.0 (dt, J=7.2, 15.5 Hz, 1H), 7.31-7.40 (m, 5H), 8.21-8.33 (m, 4H); $^{13}$C NMR ($CDCl_3$, 50 M Hz): δ14.0 (q), 14.2 (q), 22.6 (t), 25.1 (t), 31.1(t), 31.9 (t), 34.5 (t), 36.6 (t), 60.3 (t), 73.0 (t), 79.3 (d), 80.7 (d), 81.7 (d), 82.6 (d), 123.6 (d, 2C), 124.1 (d), 127.5 (d), 128.0 (d, 2C), 128.3 (d, 2C), 130.7 (d, 2C), 135.0 (s), 138.7 (s), 143.7 (d), 150.6 (s), 164.2 (s), 166.1 (s) ppm; HRMS (ESI+) calculated for $C_{30}H_{37}NO_8Na$ 562.2519, found 562.2405.

Example 12

Synthesis of (2R,3S,5R)-2-(4-Ethoxy-4-oxobutyl)-5-((R)-1-hydrioxyhehyl)tetrahydrofuran-3-yl-4-aminobenzoate (14)

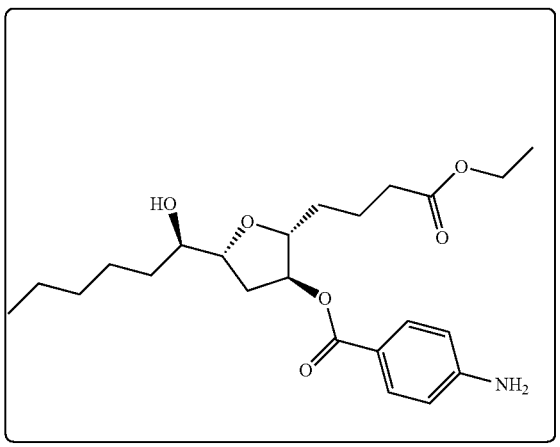 [SMILES: CCCCC[C@@H](O)[C@H]1C[C@H](OC(=O)c2ccc(N)cc2)[C@@H](CCCC(=O)OCC)O1]

The same procedure as in the preparation of 11 was used with the ester 13 (120 mg, 0.21 mmol), gave ester 14 (83 mg, 88%) as colourless oil. $R_f$ 0.5 (30% EtOAc in petroleum ether); $[\alpha]_D^{25}$+12.8 (c1.0, CHCl$_3$); $^1$H NMR (CDCl$_3$, 200 M Hz): δ 0.90 (t, J=6.3 Hz, 3H), 1.26 (t, J=7.0 Hz, 3H), 1.32-1.54 (m, 8H), 1.55-1.69 (m, 2H), 1.70-1.86 (m, 2H), 2.02-2.11 (m 2H), 2.37 (td, J=2.9, 6.9 Hz, 2H), 3.46 (dt, J=4.6, 9.5 Hz, 1H), 4.01-4.08 (m, 2H), 4.14 (q, J=7.0 Hz, 2H), 5.15 (dt, J=2.1, 5.1 Hz, 1H), 6.61-6.68 (m, 2H), 7.81-7.88 (m, 2H); $^{13}$C NMR (CDCl$_3$, 50 M Hz): δ14.0 (q), 14.2 (q), 21.3 (t), 22.6 (t), 25.4 (t), 31.8 (t), 33.5 (t), 33.9 (t), 34.0 (t), 34.2 (t), 60.4 (t), 73.6(d), 78.8 (d), 81.9 (d), 84.0 (d), 113.7 (d, 2C), 119.3 (s), 131.7 (d, 2C), 151.0 (s), 166.1 (s), 173.5 (s) ppm; HRMS (ESI+) calculated for $C_{23}H_{35}NO_6Na$ 444.2464, found 444.2352.

Example 13

Synthesis of 5-epi-(+)-Petromyroxol (2)

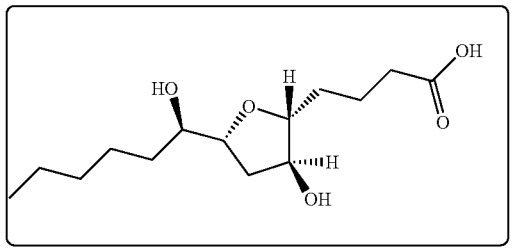 [SMILES: CCCCC[C@@H](O)[C@H]1C[C@H](O)[C@@H](CCCC(=O)O)O1]

The same procedure as in the preparation of 1 was used with the ester 14 (60 mg, 0.16 mmol) afford 5-epi-(+)-Petromyroxol (2) (29 mg, 74%) as colourless oil. $R_f$ 0.2 (100% AcOEt); $[\alpha]_D^{25}$+9.9 (c3.6, CHCl$_3$); $^1$H NMR (CDCl$_3$, 400 M Hz): δ 0.90 (t, J=6.8 Hz, 3H), 1.27-1.39 (m, 5H), 1.41-1.53 (m, 4H), 1.56-1.64 (m, 1H), 1.65-1.76 (m, 1H), 1.80 (m, 1H), 1.86 (ddd, J=2.3, 6.1, 13.2 Hz, 1H), 1.95 (ddd, J=6.0, 9.4, 15.4 Hz, 1H), 2.34-2.48 (m, 2H), 3.41 (ddd, J=3.3, 5.0, 9.5 Hz, 1H), 3.80 (ddd, J=2.4, 4.8, 7.8 Hz, 1H), 4.05 (ddd, J=5.0, 6.7, 11.3 Hz, 1H), 4.10 (dt, J=2.4, 5.4 Hz, 1H); $^{13}$C NMR (CDCl$_3$, 100 M Hz): δ14.0 (q), 21.1 (t), 22.6 (t), 25.3 (t), 31.8 (t), 33.3 (t), 33.5 (t), 33.7 (t), 36.7 (t), 74.0 (d), 76.2 (d), 81.3 (d), 86.1 (d), 177.7 (s) ppm; HRMS (ESI+) calculated for $C_{14}H_{26}O_5Na$ 297.1780, found 297.1688.

Example 14

Synthesis of Ethyl (E)-4-((2S,3R,5R)-3-acetoxy-5-((R)-1-(benzyloxy)hexyl)tetrahydrofuran-2-yl)but-2-enoate (15)

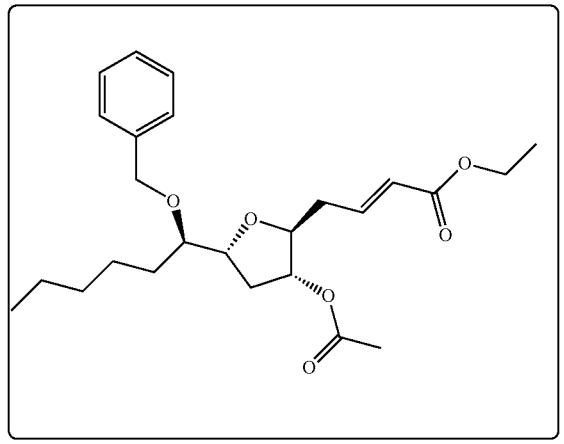 [SMILES: CCCCC[C@@H](OCc1ccccc1)[C@H]1C[C@@H](OC(C)=O)[C@H](C/C=C/C(=O)OCC)O1]

The same procedure as in the preparation of 5 was used with the acetate 10β-Ac (150 mg, 0.4 mmol) gave ester 15 (125 mg, 69% over 2 steps) as colourless oil. $R_f$ 0.5 (20% EtOAc in petroleum ether); $[\alpha]_D^{25}$−10.3 (c1.7, CHCl$_3$); $^1$H NMR (CDCl$_3$, 500 M Hz): δ 0.88 (t, J=7.0 Hz, 3H), 1.28 (t, J=7.3 Hz, 3H), 1.23-1.49 (m, 8H), 1.81 (ddd, J=5.5, 7.6, 13.1 Hz, 1H), 2.04 (s, 3H), 2.40 (dt, J=7.3, 13.7 Hz, 1H), 2.44-2.53 (m, 2H), 3.42 (q, J=5.8 Hz, 1H), 4.10 (dt, J=5.2, 9.8 Hz, 1H), 4.15 (dd, J=7.9, 14.3 Hz, 1H), 4.19 (q, J=7.0 Hz, 2H), 4.63 (d, J=11.6 Hz, 1H), 4.72 (d, J=11.6 Hz, 1H), 4.92 (ddd, J=4.0, 5.2, 9.7 Hz, 1H), 5.93 (d, J=15.6 Hz, 1H), 6.97 (dt, J=7.0, 15.6 Hz, 1H), 7.26-7.38 (m, 5H) ; $^{13}$C NMR (CDCl$_3$, 125 M Hz): δ14.0 (q), 14.2 (q), 21.0 (q), 22.6 (t), 25.2 (t), 30.7 (t), 31.9 (t), 34.0 (t), 35.4 (t), 60.2 (t), 72.9 (t), 77.4 (d), 80.1 (d), 80.5 (d), 80.9 (d), 123.8 (d), 127.5 (d), 127.9 (d, 2C), 128.2 (d, 2C), 138.8 (d), 144.0 (d), 166.2 (s), 170.7 (s) ppm; HRMS (ESI+) calculated for $C_{25}H_{36}O_6Na$ 455.2512, found 455.2398.

Example 15

Synthesis of Ethyl-4-((2S,3R,5R)-3-acetoxy-5-((R)-1-hydroxyhexyl)tetrahydrofuran-2-yl)butan-oate (16)

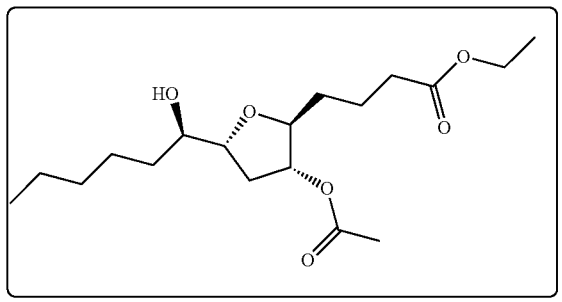 [SMILES: CCCCC[C@@H](O)[C@H]1C[C@@H](OC(C)=O)[C@H](CCCC(=O)OCC)O1]

The same procedure as in the preparation of 11 was used with the ester 15 (100 mg, 0.23 mmol) gave ester 16 (73 mg, 92%) as colourless oil. $R_f$ 0.6 (30% EtOAc in petroleum ether): $[\alpha]_D^{25}$ −11.0 (c1.1, CHCl$_3$); $^1$H NMR (CDCl$_3$, 200 M Hz): δ 0.89 (t, J=6.4 Hz, 3H), 1.26 (t, J=7.0 Hz, 3H) 1.30-1.59 (m, 8H), 1.63-1.73 (m, 2H), 1.74-1.84 (m, 2H), 2.06 (s, 3H), 2.34 (t, J=7.3 Hz, 2H), 2.43 (dd, J=7.4, 14.6 Hz, 2H), 3.51 (dt, J=5.7, 10.1 Hz, 1H), 3.87 (ddd, J=6.5, 6.5, 12.8 Hz, 1H), 3.97 (ddd, J=3.4, 5.6, 8.2 Hz, 1H), 4.13 (q, J=7.0 Hz, 2H), 4.93 (ddd, J=3.8, 3.8, 7.2 Hz, 1H); $^{13}$C NMR (CDCl$_3$, 50 M Hz): δ14.0 (q), 14.2 (q), 21.1 (q), 21.2 (t), 22.6 (t), 25.3 (t), 31.8 (t, 2C), 33.2 (t), 33.9 (t, 2C), 60.3 (t), 73.5 (d), 78.2 (d), 80.5 (d), 82.5 (d), 170.6 (s), 173.4 (s) ppm; HRMS (ESI+) calculated for C$_{18}$H$_{32}$O$_6$Na 367.2199, found 367.2086.

Example 16

Synthesis of 6-epi-(+)-Petromyroxol (3)

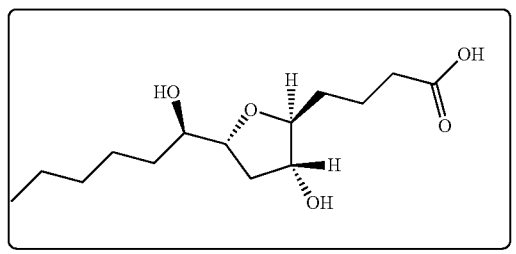 [SMILES: CCCCC[C@@H](O)[C@H]1C[C@@H](O)[C@H](CCCC(=O)O)O1]

The same procedure as in the preparation of 1 was used with the ester 16 (60 mg, 0.17 mmol) afford 6-epi-(+)-Petromyroxol (3) (37 mg, 77%) as colourless oil. $R_f$ 0.2 (100% EtOAc); $[\alpha]_D^{25}$ −27.6 (c 0.6, CHCl$_3$); $^1$H NMR (CDCl$_3$, 400 M Hz): δ 0.89 (t, J=6.6 Hz, 3H), 1.27-1.32 (m, 3H), 1.33-1.39 (m, 2H), 1.41-1.47 (m, 2H), 1.48-1.52 (m, 2H), 1.53-1.74 (m, 2H), 1.75-1.82 (m, 2H), 2.35 (dd, J=6.3, 8.9 Hz, 1H), 2.39 (t, J=7.3 Hz, 2H), 3.51 (ddd, J=3.2, 4.8, 8.8 Hz, 1H), 3.91 (ddd, J=2.2, 5.2, 8.5 Hz, 1H), 4.0 (ddd, J=2.9, 5.2, 9.3 Hz, 1H), 4.04 (ddd, J=2.0, 3.2, 6.3 Hz, 1H); $^{13}$C NMR (CDCl$_3$, 100 M Hz): δ14.0 (q), 21.0 (t), 22.6(t), 25.5 (t), 31.7 (t), 32.3 (t), 33.6 (t), 33.8 (t), 36.9 (t), 74.1 (d), 75.3 (d), 79.7 (d), 86.3 (d), 178.0 (s) ppm ; HRMS (ESI+) calculated for C$_{14}$H$_{26}$O$_5$Na 297.1780, found 297.1668.

Example 17

Synthesis of Ethyl (E)-4-((2R,3R,5R)-3-acetoxy-5-((R)-1-(benzyloxy)hexyl)tetrahydrofuran-2-yl)but-2-enoate (17)

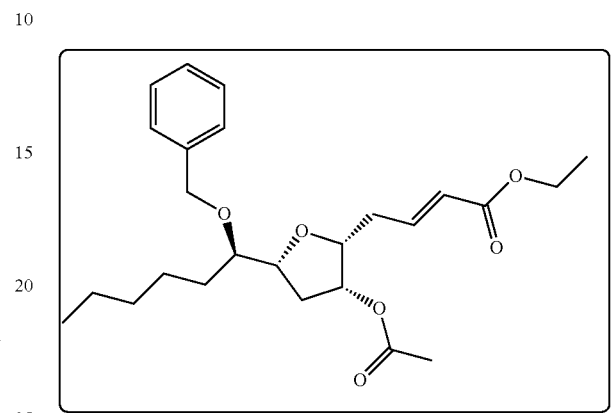

The same procedure as in the preparation of 5 was used with the ester 10α-Ac (250 mg, 0.72 mmol) gave ester 17 (208 mg, 69% over 2 steps) as colourless syrup. $R_f$ 0.5 (20% EtOAc in petroleum ether); $[\alpha]_D^{25}$+5.2 (c 0.4, CHCl$_3$); $^1$H NMR (CDCl$_3$, 500 M Hz): δ 0.89 (t, J=7.0 Hz, 3H), 1.28 (t, J=7.0 Hz, 3H), 1.23-1.50 (m, 8H), 1.71 (ddd, J=3.0, 7.9, 14.3 Hz, 1H), 2.06 (s, 3H), 2.40 (dt, J=7.6, 14.6 Hz, 1H), 2.48-2.61 (m, 2H), 3.43 (dt, J=3.9, 9.5 Hz, 1H), 3.87 (dt, J=4.9, 9.5 Hz, 1H), 3.94 (q, J=7.3 Hz, 1H), 4.19 (q, J=7.0 Hz, 2H), 4.63 (d, J=11.6 Hz, 1H), 4.76 (d, J=11.6 Hz, 1H), 5.24 (dt, J=3.7, 7.3 Hz, 1H), 5.92 (d, J=15.9 Hz, 1H), 6.99 (dt, J=7.0, 14.9 Hz, 1H), 7.26-7.37 (m, 5H); $^{13}$C NMR (CDCl$_3$, 125 M Hz): δ14.0 (q), 14.2 (q), 21.0 (q), 22.6 (t), 25.2 (t), 30.9 (t), 31.9 (t), 32.2 (t), 35.8 (t), 60.3 (t), 73.1 (t), 74.4 (d), 79.5 (d), 80.6 (d), 80.7 (d), 123.3 (d), 127.5 (d,), 128.0 (d, 2C), 128.2 (d, 2C), 138.9 (s), 144.7 (d), 166.3 (s), 170.5 (s) ppm; HRMS (ESI+) calculated for C$_{25}$H$_{36}$O$_6$Na 455.2512, found 455.2401.

Example 18

Synthesis of Ethyl-4-((2R,3R,5R)-3-acetoxy-5-((R)-1-hydroxyhexyl)tetrahydrofuran-2-yl) buta-noate (18)

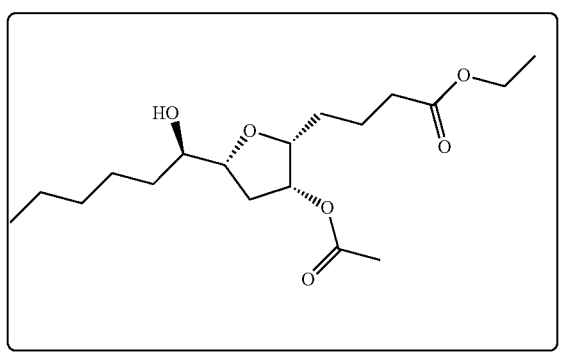 [SMILES: CCCCC[C@@H](O)[C@H]1C[C@@H](OC(C)=O)[C@@H](CCCC(=O)OCC)O1]

The same procedure as in the preparation of 11 was used with the ester 17 (150 mg, 0.32 mmol) gave ester 18 (109 mg, 91%) as colourless oil. R$_f$ 0.5 (30% EtOAc in petroleum ether): [α]$_D^{25}$–4.3 (c 0.3, CHCl$_3$); $^1$H NMR (CDCl$_3$, 400 M Hz): δ 0.90 (t, J=6.8 Hz, 3H), 1.27 (t, J=7.0 Hz, 3H), 1.28-1.56 (m, 8H), 1.61-1.1.72 (m, 3H), 1.73 -1.84 (m, 2H), 2.07 (s, 3H), 2.36 (t, J=7.3 Hz, 2H), 2.41 (dd, J=6.6, 8.0 Hz, 1H), 3.47 (bs, 1H), 3.74-3.79 (m, 2H), 4.14 (q, J=7.0 Hz, 2H), 5.23 (ddd, J=2.2, 3.9, 6.4 Hz, 1H) ; $^{13}$C NMR (CDCl$_3$, 100 M Hz): δ14.0 (q), 14.2 (q), 21.0 (q), 21.8 (t), 22.6 (t), 25.3 (t), 28.3 (t), 31.8 (t), 33.6 (t), 34.1 (t), 35.7 (t), 60.3 (t), 73.7 (d), 74.8 (d), 80.6 (d), 81.3 (d), 170.5 (s), 173.4 (s) ppm; HRMS (ESI+) calculated for C$_{18}$H$_{32}$O$_6$Na 367.2199, found 367.2091.

Example 19

Synthesis of 5,6-bis-epi-(+)-Petromyroxol (4)

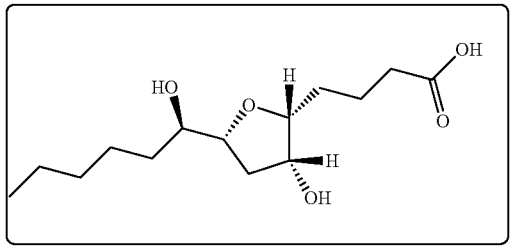 [SMILES: CCCCC[C@@H](O)[C@H]1C[C@@H](O)[C@@H](CCCC(=O)O)O1]

The same procedure as in the preparation of 1 was used with the ester 18 (80 mg, 0.23 mmol) afford 5,6-bis-epi-(+)-Petromyroxol (4) (48 mg, 75%) as colourless oil. R$_f$ 0.2 (100% EtOAc); [α]$_D^{25}$–14.9 (c0.2, CHCl$_3$); $^1$H NMR (CDCl$_3$, 500 M Hz): δ 0.90 (t, J=6.4 Hz, 3H), 1.28-1.30 (m, 2H), 1.31-1.33 (m, 2H), 1.34-1.38 (m, 2H), 1.51-164 (m, 2H), 1.66-1.80 (m, 4H), 1.89 (dd, J=3.3, 14.1 Hz, 1H), 2.39 (ddd, J=4.9, 8.9, 14.0 Hz, 1H), 2.43 (t, J=6.4 Hz, 2H), 3.50 (ddd, J=2.2, 4.8, 7.2 Hz, 1H),3.67 (ddd, J=2.9, 6.1, 9.0 Hz, 1H), 4.0 (dt, J=2.3, 9.7 Hz, 1H), 4.12 (dd, J=2.9, 5.2 Hz, 1H) ; $^{13}$C NMR (CDCl$_3$, 125 MHz): δ14.0 (q), 21.3 (t), 22.6 (t), 25.6 (t), 28.0 (t), 31.7 (t), 33.6 (t), 34.2 (t), 38.3 (t), 71.6 (d), 73.9 (d), 79.3 (d), 83.8 (d), 177.3 (s)ppm ; HRMS (ESI+) calculated for C$_{14}$H$_{26}$O$_5$Na 297.1780, found 297.1667.

ADVANTAGES OF INVENTION

1. Simple and cost-effective process
2. Easily available raw materials and Easily scalable
3. Access to the other diastereomers
4. Chiral pool approach

We claim:

1. A process for synthesis of (+)-petromyroxol or diastereomers thereof, comprising the steps of:
   a) subjecting the epoxide (3aR,5R,6aR)-2,2-dimethyl-5-((R)-oxiran-2-yl)tetrahydrofuro[2,3-d][1,3]dioxole to ring opening in the presence of n-BuLi to afford alcohol (S)-1-((3aR,5R,6aR)-2,2-dimethyltetrahydrofuro[2,3-d][1,3]dioxol-5-yl)hexan-1-ol;
   b) benzylating the free —OH group of the alcohol of step (a) in the presence of NaH and benzyl bromide in THF to afford benzylether (3aR,5R,6aR)-5-((S)-1-(benzyloxy)hexyl)-2,2-dimethyltetrahydrofuro[2,3-d][1,3]dioxole;
   c) subjecting the benzylether of step (b) to C-allylation with allyltrimethylsilane in the presence of BF$_3$·Et$_2$O in dichloromethane to afford a mixture of α- and β-C-allylglycosides (2R,3R,5R)-2-allyl-5-((S)-1-(benzyloxy)hexyl)tetrahydrofuran-3-ol-α and (2S,3R,5R)-2-allyl-5-((S)-1-(benzyloxy)hexyl)tetrahydrofuran-3-ol-β;
   d) subjecting one or the other allylglycosides of step (c) to acetylation to afford the corresponding acetate of (2R,3R,5R)-2-allyl-5-((S)-1-(benzyloxy)hexyl)tetrahydrofuran-3-ol-α or (2S,3R,5R)-2-allyl-5-((S)-1-(benzyloxy)hexyl)tetrahydrofuran-3-ol-β; or
   e) subjecting the (2R,3R,5R)-2-allyl-5-((S)-1-(benzyloxy)hexyl)tetrahydrofuran-3-ol-α or (2S,3R,5R)-2-allyl-5-((S)-1-(benzyloxy)hexyl)tetrahydrofuran-3-ol-β of step (c) to a Mitsunobu reaction in the presence of p-nitrobenzoic acid, diisopropylazodicarboxylate, and triphenylphosphine in dichloromethane to afford the corresponding benzoate;
   f) subjecting a benzoate of step (e) or acetate of step (d) to oxidative olefin cleavage in the presence of OsO$_4$ and NaIO$_4$ to afford an intermediate aldehyde, followed by two-carbon Wittig homologation of said aldehyde to afford a corresponding unsaturated ester;
   g) hydrogenating the unsaturated ester of step (f) to afford the corresponding saturated ester; and
   h) subjecting the saturated ester of step (g) to saponification using base in solvent to afford (+)-petromyroxol or diastereomers thereof.

2. The process as claimed in claim 1, wherein said diastereomers are selected from 5-epi-(+)-petromyroxol, 6-epi-(+)-petromyroxol, and 5,6-bis-epi-(+)-petromyroxol.

3. The process as claimed in claim 1, wherein the acetylation in step (d) is carried out using acetic anhydride as acylating agent in presence of dimethylaminopyridine as a catalyst.

4. The process as claimed in claim 1, wherein said two-carbon Wittig homologation in step (f) is carried out using ethyl 2-(triphenyl-λ$^5$-phosphanylidene) acetate.

5. The process as claimed in claim 1, wherein the hydrogenation in step (g) is carried out under an H$_2$ atmosphere and in the presence of Pearlman's catalyst.

6. The process as claimed in claim 1, wherein said base in step (h) is selected from potassium hydroxide and sodium hydroxide.

7. The process as claimed in claim 1, wherein said solvent in step (h) is selected from methanol, ethanol, propanol and butanol.

8. The process as claimed in claim 1, wherein said benzoate in step (e) is (2S,3S,5R)-5-((R)-1-(benzyloxy)hexyl)tetrahydrofuran-3-yl-4-nitrobenzoate.

9. The process as claimed in claim 1, wherein said unsaturated ester in step (f) is selected from (2S,3S,5R)-5-((R)-1-(benzyloxy)hexyl)-2-((E)-4-ethoxy-4-oxobut-2-en-1-yl)tetrahydro-furan-3-yl-4-nitrobenzoate, (2R,3S,5R)-5-((R)-1-(benzyloxy)hexyl)-2-((E)-4-ethoxy-4-oxobut-2-en-1-yl)tetrahydro-furan-3-yl-4-nitrobenzoate, ethyl (E)-4-((2S,3R,5R)-3-acetoxy-5-((R)-1-(benzyloxy)hexyl) tetrahydrofuran-2-yl)but-2-enoate, and ethyl (E)-4-((2R,3R,5R)-3-acetoxy-5-((R)-1-(benzyloxy)hexyl)tetrahydrofuran-2-yl) but-2-enoate.

10. The process as claimed in claim 1, wherein said saturated ester in step (g) is selected from (2S,3S,5R)-2-(4-ethoxy-4-oxobutyl)-5-((R)-1-hydroxyhexyl)tetrahydro-furan-3-yl-4-aminobenzoate, (2R,3S,5R)-2-(4-ethoxy-4-oxobutyl)-5-((R)-1-hydroxyhexyl)tetrahydrofuran-3-yl-4-aminobenzoate, ethyl-4-((2S,3R,5R)-3-acetoxy-5-((R)-1- hydroxyhexyl)tetrahydrofuran-2-yl)butanoate, and ethyl-4-((2R,3R,5R)-3-acetoxy-5-((R)-1-hydroxyhexyl)tetrahydrofuran-2-yl)butanoate.